(12) United States Patent
Olson et al.

(10) Patent No.: US 7,917,204 B2
(45) Date of Patent: Mar. 29, 2011

(54) METHOD AND IMPLANTABLE MEDICAL DEVICE FOR MEASURING AN ELECTRICAL BIO-IMPEDANCE OF A PATIENT

(75) Inventors: Allan Olson, Spånga (SE); Louis Wong, Sunnyvale, CA (US)

(73) Assignee: St. Jude Medical AB, Jarfalla (SE)

( * ) Notice: Subject to any disclaimer, the term of this patent is extended or adjusted under 35 U.S.C. 154(b) by 408 days.

(21) Appl. No.: 12/088,996

(22) PCT Filed: Oct. 11, 2005

(86) PCT No.: PCT/SE2005/001530
§ 371 (c)(1),
(2), (4) Date: Apr. 2, 2008

(87) PCT Pub. No.: WO2007/043923
PCT Pub. Date: Apr. 19, 2007

(65) Prior Publication Data
US 2008/0221477 A1    Sep. 11, 2008

(51) Int. Cl.
*A61B 5/053* (2006.01)
(52) U.S. Cl. .................................... 600/547
(58) Field of Classification Search .............. 600/547
See application file for complete search history.

(56) References Cited

U.S. PATENT DOCUMENTS

| 5,534,018 | A | 7/1996 | Wahlstrand et al. |
| 5,713,935 | A | 2/1998 | Prutchi et al. |
| 5,957,861 | A | 9/1999 | Combs et al. |
| 6,044,294 | A | 3/2000 | Mortazavi et al. |
| 6,076,015 | A | 6/2000 | Hartley et al. |
| 6,104,949 | A | 8/2000 | Pitts Crick et al. |
| 6,208,898 | B1 | 3/2001 | Gliner et al. |
| 6,269,264 | B1 * | 7/2001 | Weyant et al. ............... 600/547 |
| 6,511,438 | B2 | 1/2003 | Bernstein et al. |
| 7,024,241 | B1 | 4/2006 | Bornzin |
| 2002/0040192 | A1 | 4/2002 | Prutchi |
| 2006/0100539 | A1 * | 5/2006 | Min et al. ...................... 600/547 |

FOREIGN PATENT DOCUMENTS
WO    WO 2004/052198    * 6/2004

* cited by examiner

*Primary Examiner* — Max Hindenburg
*Assistant Examiner* — Michael C Stout
(74) *Attorney, Agent, or Firm* — Schiff Hardin LLP

(57) ABSTRACT

In a method and device for measuring an electrical bio-impedance of a patient at least one impedance measurement signal is generated by a current pulse generator, the signal having at least one asymmetric multiphasic impedance measurement waveform that is asymmetric in term of pulse amplitude and/or pulse width relative to the operating voltage of the current pulse generator. The waveform has a DC component that is substantially equal to zero, and is adapted to the available voltage headroom of an implantable device that contains the current pulse generator. The impedance measurement signal with the aforementioned waveform is applied to a patient and a resulting impedance signal is produced thereby, from which at least one impedance value is determined.

13 Claims, 4 Drawing Sheets

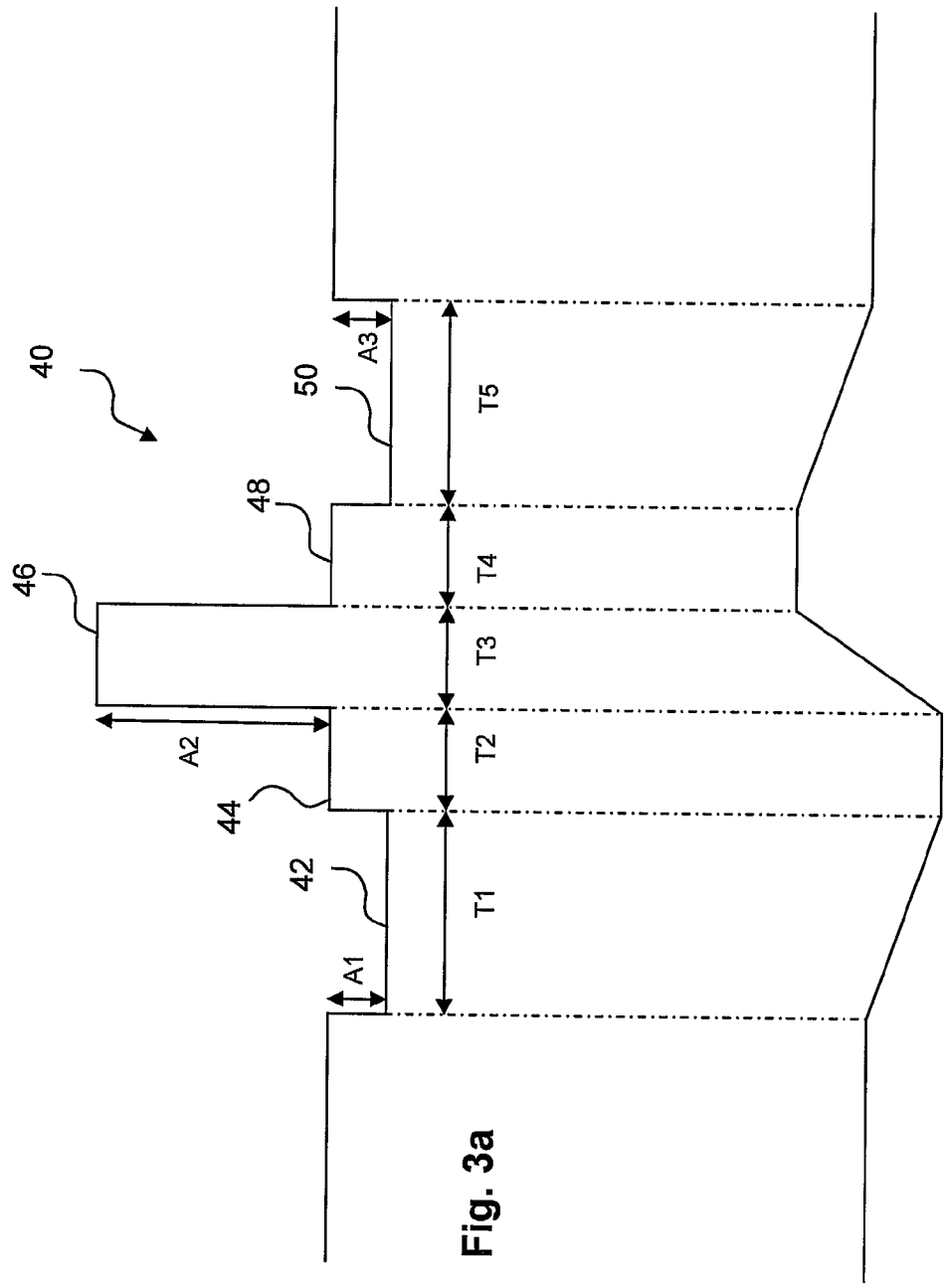

METHOD AND IMPLANTABLE MEDICAL DEVICE FOR MEASURING AN ELECTRICAL BIO-IMPEDANCE OF A PATIENT

BACKGROUND OF THE INVENTION

1. Field of the Invention

The present invention generally relates to implantable medical devices, such as cardiac pacemakers and implantable cardioverter/defibrillators, and in particular to an improved method and medical device for measuring electrical bio-impedance signals:

2. Description of the Prior Art

Electrical bio-impedance signals has been found to be an useful tool in implantable medical devices, such as cardiac pacemakers. For example, electrical bio-impedance signals can be used to determine the amount of air being inhaled by a patient to assess the patient's need for cardiac output in order to provide a proper pacing pulse rate to the patient since measuring the impedance of the chest cavity has been found to provide a good indication of the amount of air being inhaled by a patient. One example of this is described in U.S. Pat. No. 5,197,467. Furthermore, electrical bio-impedance has been found to be an effective measure for identifying changes of many different conditions in the body of a patient, such as incipient pulmonary edema and the progression of pulmonary edema due to CHF. For example, the accumulation of fluids in the lung-region associated with pulmonary edema affects the thoracic impedance, since the resistivity of the lung changes in accordance with a change of the ratio of fluid to air. As indicated in U.S. Pat. No. 5,957,861, it is possible to detect pulmonary edema at an early stage by means of transthoracic impedance measured by an implanted device such as a pacemaker.

In addition to the thoracic impedance, the cardiogenic impedance, which is defined as the impedance or resistance variation that origins from cardiac contractions measured by electrodes inside or on the surface of the body, can be used for identifying changes different conditions in the heart of a patient. The cardiogenic impedance variation correlates to the volume changes of the heart chambers, which can be used as an indication of the dynamic blood filling. Hence, changes of parameters such as left ventricular ejection time (LVET) can be detected by monitoring or detecting changes of the cardiogenic impedance, see, for example U.S. Pat. No. 6,511,438.

Accordingly, a reliable and accurate method for measuring or detecting electrical bio-impedances, such as the intrathoracic impedance or the cardiogenic impedance, i.e. the cardiac component of an impedance signal measured over the heart, in an implantable medical device would be of a great value.

Conventionally, when generating multi-phasic impedance measurement current pulses, a positive and a negative current of equal amplitude and width has been used in order to only make use of fully balanced signals, i.e. integrating over the complete current pulse should ideally give a zero area. It is believed that a multi-phasic, for example, a biphasic excitation pulse offers the advantages over a monophasic pulse that the peak amplitude of the excitation pulse is minimized given the overall energy content of the pulse, electrode polarization is cancelled, and DC current is balanced to avoid long-term lead metal-ion oxidation, see, for example, U.S. Pat. Nos. 6,269,264, and 6,104,949. However, since the pulse generator of a conventional implantable medical device, such as a pacemaker, typically operates around 0.50.9 V with the case or housing of the device as the negative supply, i.e. 0 V, and the battery (about −2.8 V) as the positive supply, the negative voltage headroom is significantly lower than the positive headroom. The current pulse amplitude is hence limited by the negative voltage headroom (negative available voltage) and the complete potential operating range of the pulse generator is not utilized. This may, in turn, entail to an impaired signal-to-noise ratio of the measured impedance signal.

Accordingly, there is a need of an improved method and medical device that are able to obtain reliable and accurate electrical bio-impedance signals.

SUMMARY OF THE INVENTION

Thus, an object of the present invention is to provide an improved method and medical device that are able to obtain more reliable and accurate electrical bio-impedance signals.

In the context of this application, the term "impedance" refers to the DC component of the impedance. The measured impedance consists of a DC component and an AC component, where the DC component is the baseline around which the AC component fluctuates. The DC component reflects the amount of tissue and fluids that are located between the measuring points that the impedance is measured in-between and the AC components reflects how respiration and cardiac activity influence the impedance signal.

For clarity, the term "intrathoracic impedance" refers to an impedance measurement over the thorax by using an implantable medical device, i.e. an impedance measurement where the impedance measurement vector spans over the thorax.

Moreover, in order to clarify, the term "cardiogenic impedance" is defined as the impedance or resistance variation that origins from cardiac contractions or, in other words, the cardiac component of the impedance measured between electrodes within the heart.

According to an aspect of the present invention, there is provided a method for measuring an electrical bio-impedance of a patient with an implanted medical device including at least one electrode configuration, comprising the steps of initiating an electrical bio-impedance measurement session, wherein at least one impedance measurement signal is generated; applying the generated at least one impedance measurement signal to the patient using the at least one electrode configuration; measuring at least one resulting impedance signal produced by the applied at least one impedance measurement signal; and determining at least one impedance value using the measured impedance signal. At least one asymmetric multiphasic impedance measurement waveform is generated in order to produce the impedance measurement signal, the at least one asymmetric multiphasic impedance measurement waveform having a DC component being substantially equal to zero. The waveform is generated by a current pulse generator operating with an operating voltage, and the at least one asymmetric waveform is asymmetric in terms of pulse amplitude and/or pulse width relative to the operating voltage of the current pulse generator. Moreover, the at least one asymmetric waveform is adapted to the available voltage headroom of the implantable device.

According to a second aspect of the present invention, there is provided an implantable medical device for measuring an electrical bio-impedance of a patient with an implanted medical device having at least one electrode configuration, comprising: a control circuit; an impedance circuit connected to the control circuit, which control circuit is adapted to influence the impedance circuit to initiate an electrical bio-impedance measurement session, wherein at least one impedance measurement signal is generated and applied to the patient using the at least one electrode configuration; a voltage signal measurement circuit connected to the control circuit and adapted to measure at least one resulting impedance signal produced by the applied at least one impedance measurement signal; and wherein the control circuit being adapted to determine at least one impedance value using the measured impedance signal. The medical device is characterized by the control circuit being configured to influence the impedance circuit to generate at least one asymmetric multiphasic impedance measurement waveform in order to generate the impedance measurement signal, wherein the at least one asymmetric multiphasic impedance measurement waveform has a DC component being substantially equal to zero.

According to a third aspect of the present invention, there is provided a computer readable medium encoded with programming instructions that cause a computer to perform a method as described above.

Thus, the invention is based on the use of asymmetrical current waveforms thereby making it possible to utilize, in principle, substantially the complete potential positive voltage headroom as the same time as the waveforms has a zero DC component. In other words, by generating pulses being asymmetric in terms of pulse magnitude or amplitude and/or pulse width about the operating voltage of the current pulse generator, it is possible to make use of the positive voltage headroom and still obtain a fully balanced impedance measurement signal. The asymmetric pulses thus enable a more efficient usage of the operating range of the current pulse generator.

This solution provides several advantages over the existing solutions. One advantage is that an improved signal-to-noise ratio can be obtained in comparison to the known technique due to the fact that the total energy content of the impedance measurement signal can be increased.

Another advantage is that the impedance measurement signal according to the present invention does not create significant interference in the low frequency range in which, for example, typical ECG machines are sensitive since the generated signal has a zero DC component. Hence, interference with an external device, such as an ECG machine, can be minimized.

In one embodiment, the at least one asymmetric multiphasic impedance measurement waveform comprises a number of pulses having predetermined asymmetrically distributed pulse amplitudes and pulse widths with respect to an operating voltage of the current pulse generator of the medical device.

In accordance with one embodiment of the present invention, at least one null period having a predetermined length is generated, wherein the null period is intermediate to two successive pulses.

According to another embodiment, at least one asymmetric pentaphasic impedance measurement waveform is generated by: generating a first pulse of a predetermined first amplitude and a predetermined first pulse width; generating a first null period immediately following the first period and having a predetermined period length; generating a second pulse immediately following the fast null period, the second pulse being of a reversed polarity to the first pulse and having a predetermined second amplitude and a predetermined second pulse width; generating a second null period immediately following the second pulse and having the predetermined period length; and generating a third pulse immediately following the second null period, the third pulse being of a reversed polarity to the second pulse and having the predetermined first amplitude and a predetermined first pulse width. This waveform has been found to be particularly suitable in respect of, for example, usage of the positive voltage headroom and thus enables a more efficient usage of the operating range of the current pulse generator.

In a further embodiment, at least one asymmetric triphasic impedance measurement waveform is generated by: generating a first pulse of a predetermined fast amplitude and a predetermined first pulse width; generating a second pulse immediately following the first pulse, the second pulse being of a reversed polarity to the first pulse and having a predetermined second amplitude and a predetermined second pulse width; and generating a third pulse immediately following the second pulse, the third pulse being of a reversed polarity to the second pulse and having the predetermined first amplitude and a predetermined first pulse width. This waveform has also been found to be suitable in respect of, for example, usage of the positive voltage headroom and thus enables a more efficient usage of the operating range of the current pulse generator.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

FIG. 3a is an illustrative pentaphasic impedance measurement waveform in accordance with the present invention.

FIG. 3b illustrates the integrated area of the pentaphasic impedance measurement waveform shown in FIG. 3a;

FIG. 4a is an illustrative triphasic impedance measurement waveform in accordance with the present invention.

FIG. 4b illustrates the integrated area of the pentaphasic impedance measurement waveform shown in FIG. 4a.

BRIEF DESCRIPTION OF THE DRAWINGS

Figure 1:
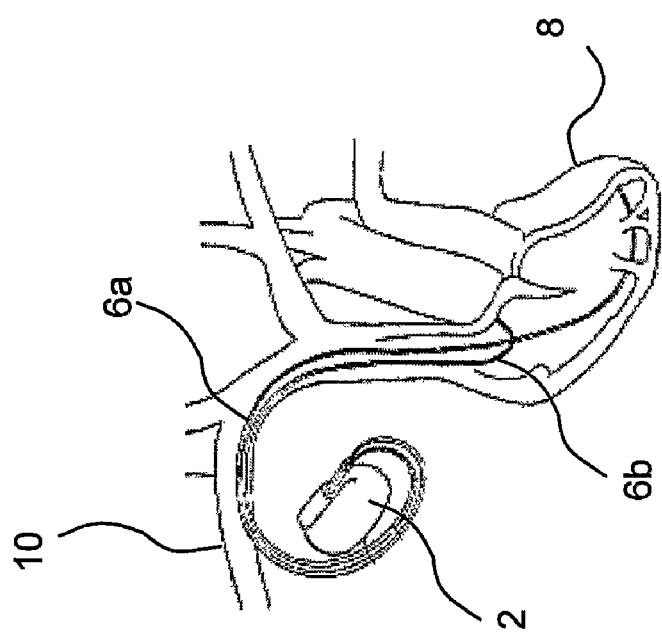
FIG. 1 is schematic diagram showing a medical device implanted in a patient in which device the present invention can be implemented.

With reference to FIG. 1 there is shown a schematic diagram of a medical device implanted in a patient in which device the present invention can be implemented. As seen, this embodiment of the present invention is shown in the context of a pacemaker 2 implanted in a patient (not shown). The pacemaker 2 comprises a housing being hermetically sealed and biological inert. Normally, the housing is conductive and may, thus, serve as an electrode. One or more pacemaker leads, where only two are shown in FIG. 1 namely a ventricular lead 6a and a trial lead 6b, are electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As the skilled man in the art realizes, the leads 6a, 6b may be implanted with its distal end located in either the atrium or ventricle of the heart 8. Impedance measurements signals may be applied suing an electrode on one of the cardiac leads 6a, 6b and the housing or case, i.e. the external housing of the pacemaker 2.

Unipolar leads have a single electrode and bipolar leads have tip and ring electrodes. If bipolar leads are being used, the impedance measurement signals may be applied to the body of the patient between a ring electrode and the housing of the pacemaker 2 and the resulting voltage signal can be measured between the tip electrode and the housing of the pacemaker 2. There are in fact a number of possible impedance configurations, i.e. ways of injecting current between two electrodes in the pacemaker and then to measure the voltage the current provokes between the electrodes. For example, impedance configurations can be uni-polar, bi-polar, tri-polar or quadro-polar. The configuration denominated as bi-polar means, in practice, a configuration where the current and the voltage is sent out and measured between the same two electrodes. When one of the electrodes used in a bi-polar measurement is the housing or the case, the configuration is called uni-polar. For example, in FIG. 1, between the housing of the pacemaker 2 and a right ventricular electrode arranged at the distal end of lead 6a. A tri-polar configuration uses three electrodes, i.e. the current injection and the voltage measurement share one electrode. As an example, the current can be sent out from the housing or the case of the medical device to a RV-tip and the voltage is measured between the case and RV-ring. In quadro-polar measurements, the current is sent out between electrodes and the voltage is measured between two entirely different electrodes, i.e. in this case there are four electrodes involved.

Figure 2:
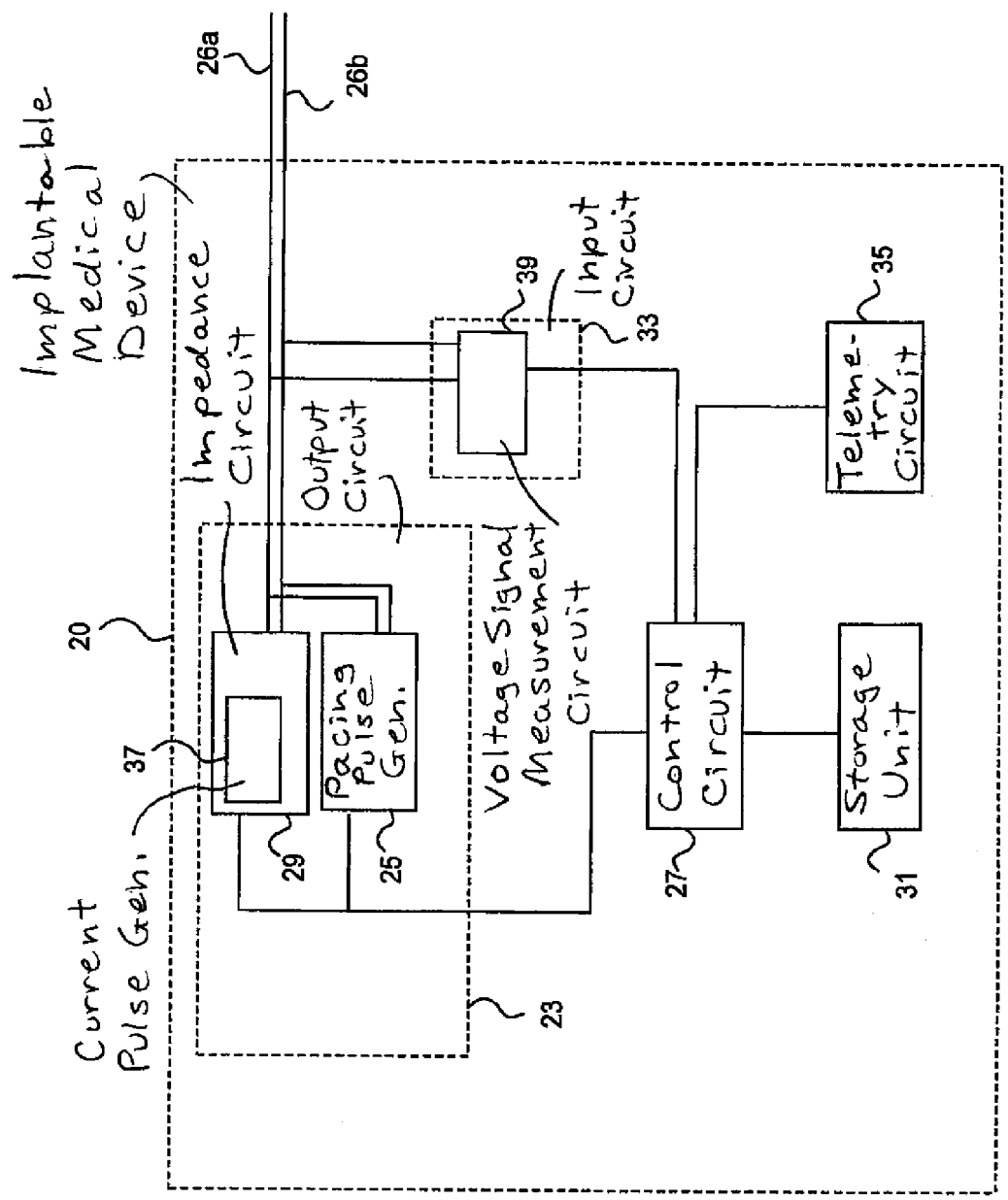
FIG. 2 is block diagram of the primary functional components of an embodiment of the present invention.

With reference now to FIG. 2, the configuration including the primary components of an embodiment of the present invention will be described. The illustrated embodiment includes an implantable medical device 20, such as the pacemaker shown in FIG. 1, and leads 26a and 26b, of the same type as the leads 6a and 6b shown in FIG. 1. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b carry one or more electrodes (as described with reference to FIG. 1), such a tip electrode or a ring electrode, arranged to, inter alia, transmit pacing pulses for causing depolarization of cardiac tissue adjacent to the electrode(-s) generated by a pacing pulse generator 25 included in an output circuit 23 under influence of a control circuit 27, which preferably is micro-processor based. The control circuit 27 controls the operation of the pacemaker 20 based on the execution of instructions stored in a memory or storage unit 31, which may include a random access memory (RAM) and/or a non-volatile memory such as a read-only memory (ROM). Detected signals from the patients heart are processed in an input circuit 33 connected to the control circuit 27. The pacemaker 20 may transmit data signals from within the patient using a telemetry circuit 35. Data signals transmitted by the telemetry circuit 35 are picked up by a conventional programmer (not shown). Various programmable parameters of the pacemaker 20 can be adjusted by a physician by sending control signals to the pacemaker 20 via the telemetry circuit 35 using the programmer.

The input circuit 33 monitors the cardiac signals of the heart 8 (see FIG. 1). Thereby, the presence of cardiac events such as, for example, P-waves or R-waves can be established. The control circuit 27 is adapted to analyze the cardiac signals monitored by the input circuit 33. Moreover, the control circuit 27 is adapted to determine whether the output circuit should apply pacing pulses to the heart 8 (see FIG. 1) and to determine pace pulse parameters such as output voltage and pulse duration.

Furthermore, the output circuit 23 includes an impedance circuit 29. The impedance circuit 29 is arranged to apply excitation current pulses between a first electrode arranged to be positioned within a heart of the patient and second electrode in an embodiment where the intrathoracic impedance is measured. The input circuit 33 is adapted to measure the resulting signal across the heart. The control circuit 27 is adapted to analyze the impedance measurement signal generated by the impedance circuit 29 and the resulting signal measured by the input circuit 33 in order to determine the impedance of the body of the patient, for example, the intrathoracic impedance. Typically, the impedance measurement signal is a current of known magnitude and the resulting signal measured across the body is a voltage signal. Alternatively, the impedance measurement signal applied to the body may be a voltage of known magnitude. If the voltage of the applied impedance measurement signal is known, the resulting magnitude of the current of the signal through the body can be measured to determine the impedance. Analyzing the impedance measurement signal and the resulting signal to determine the impedance typically involves processing these signals to determine their relative magnitudes. For example, in the absence of significant capacitive or inductive effects, the impedance of the patient's body may be calculated using Ohm's law (i.e. body impedance equals measured voltage divided by applied current).

The impedance measurement signal is preferably an AC (alternating current) impedance measurement current signal with a magnitude of 10 µA to 1000 µA generated by a current pulse generator 37 of the impedance circuit 29. Preferably, each pulses of the generated waveform has a length of about 10-80 µs Applying the impedance measurement signal over the heart 8 (see FIG. 1) via any one of the leads 26a and 26b gives rise to an impedance voltage signal, which is measured using a voltage signal measurement circuit 39 of the input circuit 33. The voltage signal measurement circuit 39 may include an AC amplifier (not shown) for amplifying the measured voltage signal and a demodulator (not shown) adapted to rectify the received signal and to provide a DC (direct current) output voltage signal. The resulting output DC voltage signal is digitized by an analog-to-digital converter (not shown) and communicated to the control circuit 27.

As described above, conventional impedance measurement signals are formed as a series of square waves, where a positive and a negative current of equal amplitude and pulse width is used in order to only make use of fully balanced signals. In other words, integrating over the complete current pulse should ideally give a zero area. However, since the pulse generator of a conventional implantable medical device, such as a pacemaker, typically operates around 0.5-0.9 V with the case or housing of the device as the negative supply, i.e. 0 V, and the battery (about −2.8 V) as the positive supply, the negative voltage headroom is significantly lower than the positive headroom. In fact, the negative voltage headroom is at minimum about 0.5 V compared to the positive voltage headroom of about 2.8-0.9=1.9 V. In contrast, in accordance to the present invention, the control circuit 27 is adapted to influence the current pulse generator 37 (FIG. 2) of the impedance circuit 29 to generate asymmetric mulliphasic waveforms, which, among other things, exhibit an improved signal-to-noise ratio and a reduced content of low frequency components in comparison with prior art.

According to an preferred embodiment of the present invention, at least one pulse having a voltage amplitude being higher that the operating voltage and having a predetermined pulse width, at least one pulse having a voltage amplitude being lower than the operating voltage and having a predetermined pulse width are generated. In this embodiment, the absolute value of the amplitude being higher that the operating voltage is not equal to an absolute value of the amplitude being lower than the operating voltage and/or the pulse width of the pulse having an amplitude being higher than the operating voltage is not equal to the pulse width of the pulse having an amplitude being lower than the operating voltage.

With reference now to FIG. 3a, an illustrative asymmetric multiphasic waveform according to an embodiment of the present invention is shown. The first portion of the waveform 40 contains a pulse 42 with a negative polarity having a pulse amplitude of A1 and a pulse width of T1. A null period 44, having a length of T2, follows immediately after the first pulse 42. Immediately thereafter, a positive pulse 46 having a pulse amplitude A2 and a pulse width T3 will follow. In a preferred embodiment, an absolute value of the amplitude A2 of the positive pulse 46 is about four times higher than an absolute value of the amplitude A1 of the negative pulse 42. Moreover, the length T3 of the positive pulse 46 is about half the length T1 of the negative pulse 42. A second null period 48 having a length of T4 follows immediately after the positive pulse 46. Preferably, the length of the second null period T4 and the length of the first null period T2 is equal. Finally, a pulse 50 with a negative polarity having a pulse amplitude A3 and a pulse width of T5 follows. Preferably, the pulse amplitude A3 and the pulse width T5 of the final pulse 50 of the waveform 40 are equal to the pulse amplitude A1 and the pulse width T1 of the first pulse 42 of the waveform 40, respectively. Suitable values for the lengths T1-T5 and amplitudes A1-A3 are about 10-80 µs and 10-1000 µA respectively.

Figures 4A, 4B:
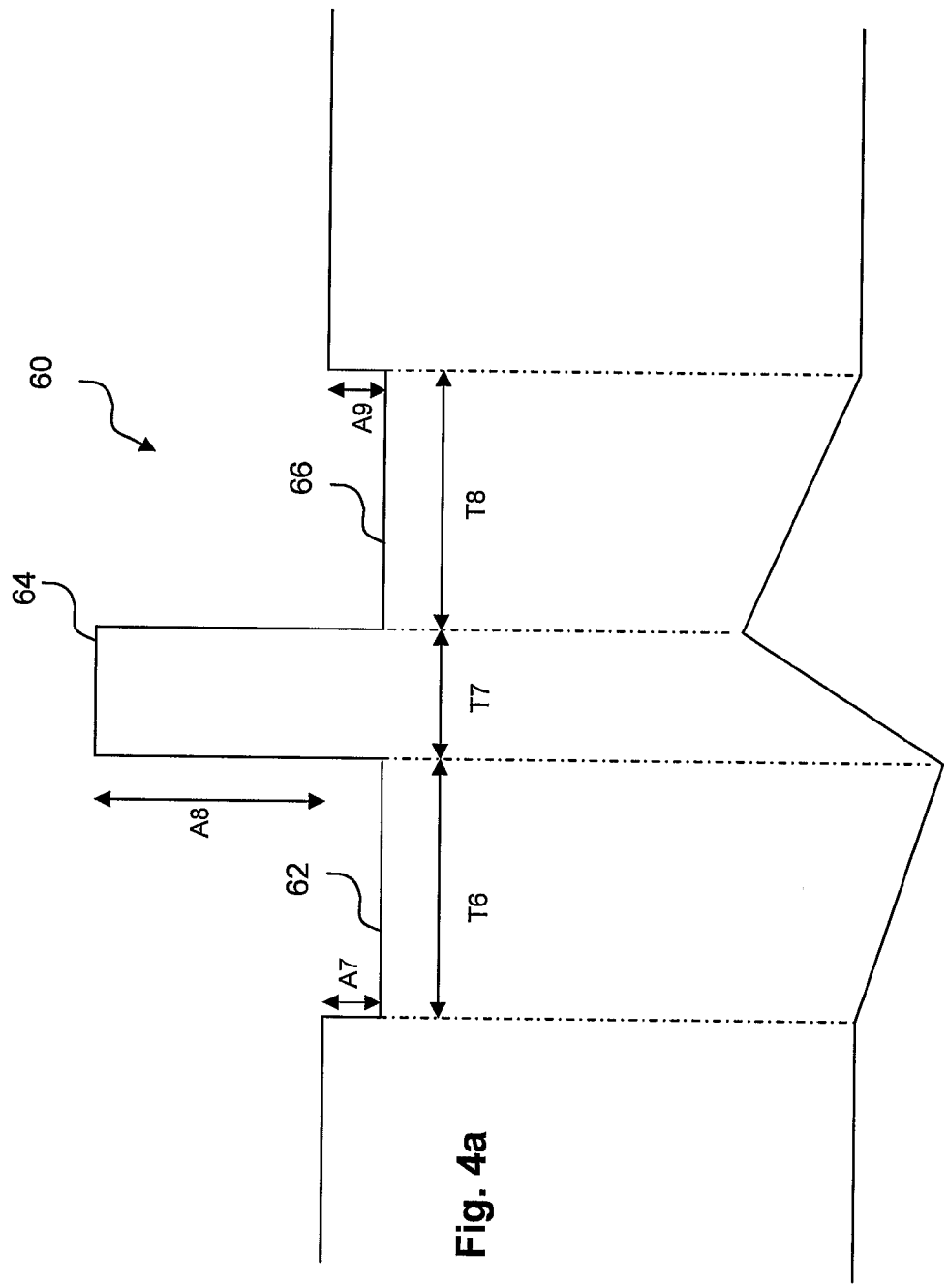

Another waveform that may be generated by the current pulse generator 37 is the triphasic waveform 60 illustrated in FIG. 4a. The waveform 60 has a negative pulse 62 of a pulse amplitude A7 and pulse width T6. A positive pulse 64 having a pulse amplitude of A8 and a pulse width of T7 follows immediately after the first pulse 62 and a second negative pulse 66 having a pulse amplitude A9 and a pulse width T8 follows after the positive pulse 64. Preferably, the amplitude A7 of the first negative pulse 62 is equal to the amplitude A9 of the second negative pulse 66. Suitable values for the lengths T7-T9 and amplitudes A7-A9 are about 10-80 µs and 10-1000 µA respectively.

As can be seen in FIGS. 3b and 4b, the pentaphasic waveform illustrated in FIG. 3a and the triphasic waveform illustrated in FIG. 4a have DC components being substantially zero, meaning a zero value after integration. Thus, at least one asymmetric multiphasic impedance measurement waveform comprising a number of pulses having predetermined asymmetrically distributed pulse amplitudes and pulse widths about an operating voltage of a pulse generator of the medical device is generated Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A method for measuring an electrical bio-impedance of a patient with an implantable medical device comprising a voltage source that provides available voltage headroom, a current pulse generator that operates at an operating voltage, and at least one electrode configuration, said method comprising the steps of:

in an electrical bio-impedance measurement session, generating, with said current pulse generator, at least one impedance measurement signal having at least one asymmetric multiphasic waveform comprised of a plurality of pulse phases each having a pulse phase amplitude, with respect to said operating voltage, and a pulse phase width, the respective pulse phase amplitudes collectively giving said waveform a waveform amplitude that is asymmetric with respect to said operating voltage, and said waveform having an overall DC component that is substantially equal to 0, and the symmetry of waveform amplitude allowing substantially all of said available voltage headroom to be used by said impedance measurement signal;

applying said at least one impedance measurement signal with said waveform to said patient using said at least one electrode configuration;

measuring at least one resulting impedance signal produced by the application of said at least one impedance measurement signal with said waveform; and determining at least one impedance value from the measured impedance signal.

2. A method as claimed in claim 1 comprising generating said at least one impedance measurement signal with said at least one asymmetric multiphasic impedance measurement waveform comprising a plurality of pulses having predetermined asymmetrically distributed respective pulse amplitudes and pulse widths with respect to said current pulse generator operating voltage.

3. A method as claimed in claim 2 comprising generating said at least one impedance measurement signal with said at least one asymmetric multiphasic impedance measurement waveform comprising at least one null period having a predetermined duration, said null period being interposed between two successive pulses of said asymmetric multiphasic impedance measurement waveform.

4. A method as claimed in claim 1 comprising generating said at least one impedance measurement signal with said asymmetric multiphasic impedance measurement waveform by:

generating a first pulse having a predetermined first pulse amplitude and a predetermined first pulse width;

generating a first null period immediately following said first pulse, said first null period having a predetermined first duration;

generating a second pulse immediately following said first null period, said second pulse having a polarity opposite to a polarity of said first pulse and having a predetermined second pulse amplitude and a predetermined second pulse width;

generating a second null period immediately following said second pulse having a predetermined second duration; and generating a third pulse immediately following said second null period, said third pulse having a polarity that is opposite to the polarity of said second pulse and having said predetermined first pulse amplitude and said predetermined first pulse width.

5. A method as claimed in claim 1 comprising generating said at least one impedance measurement signal with said asymmetric multiphasic impedance measurement waveform by:

generating a first pulse having a predetermined first pulse amplitude and a predetermined first pulse width;

generating a second pulse immediately following said first pulse, said second pulse having a polarity opposite to a polarity of said first pulse and having a predetermined second pulse amplitude and a predetermined second pulse width; and generating a third pulse immediately following said second pulse, said third pulse having a polarity that is opposite to the polarity of said second pulse and having said predetermined first pulse amplitude and said predetermined first pulse width.

6. A method as claimed in claim 1 comprising determining said at least one impedance value by analyzing a magnitude of said at least one resulting impedance signal.

7. An implantable medical device for measuring an electrical bio-impedance of a patient comprising:
a housing configured for implantation in a patient;
a voltage source in said housing that provides available voltage headroom;
a current pulse generator that operates at an operating voltage;
at least one electrode configuration; and
a control unit that, in an electrical bio-impedance measurement session, operates said current pulse generator to generate at least one impedance measurement signal having at least one asymmetric multiphasic waveform comprised of a plurality of pulse phases each having a pulse phase amplitude, with respect to said operating voltage, and a pulse phase width, the respective pulse phase amplitudes collectively giving said waveform a waveform amplitude that is asymmetric with respect to said operating voltage, and said waveform having an overall DC component that is substantially equal to 0, the asymmetry of said waveform amplitude allowing substantially all of said available voltage headroom to be used by said impedance measurement signal;
said at least one electrode configuration being configured to apply said at least one impedance measurement signal with said waveform to said patient and to detect at least one resulting impedance signal produced by the application of said at least one impedance measurement signal with said waveform, as a measured impedance signal; and
a determination unit supplied with said measured impedance signal that determines at least one impedance value from the measured impedance signal.

8. A device as claimed in claim 7 wherein said control unit operates said current pulse generator to generate said at least one impedance measurement signal with said at least one asymmetric multiphasic impedance measurement waveform comprising a plurality of pulses having predetermined asymmetrically distributed respective pulse amplitudes and pulse widths with respect to said current pulse generator operating voltage.

9. A device as claimed in claim 8 wherein said control unit operates said current pulse generator to generate said at least one impedance measurement signal with said at least one asymmetric multiphasic impedance measurement waveform comprising at least null period having a predetermined duration, said null period being interposed between two successive pulses of said asymmetric multiphasic impedance measurement waveform.

10. A device as claimed in claim 7 wherein said control unit operates said current pulse generator to generate said at least one impedance measurement signal with said asymmetric multiphasic impedance measurement waveform by generating a first pulse having a predetermined first pulse amplitude and a predetermined first pulse width, generating a first null period immediately following said first pulse, said first null period having a predetermined first duration, generating a second pulse immediately following said first null period, said second pulse having a polarity opposite to a polarity of said first pulse and having a predetermined second pulse amplitude and a predetermined second pulse width, generating a second null period immediately following said second pulse having a predetermined second duration, and generating a third pulse immediately following said second null period, said third pulse having a polarity that is opposite to the polarity of said second pulse and having said predetermined first pulse amplitude and said predetermined first pulse width.

11. A device as claimed in claim 7 wherein said control unit operates said current pulse generator to generate said at least one impedance measurement signal with said asymmetric multiphasic impedance measurement waveform by generating a first pulse having a predetermined first pulse amplitude and a predetermined first pulse width, generating a second pulse immediately following said first pulse, said second pulse having a polarity opposite to a polarity of said first pulse and having a predetermined second pulse amplitude and a predetermined second pulse width, generating a third pulse immediately following said second pulse, said third pulse having a polarity that is opposite to the polarity of said second pulse and having said predetermined first pulse amplitude and said predetermined first pulse width.

12. A device as claimed in claim 7 wherein said determination unit determines said at least one impedance value by analyzing a magnitude of said at least one resulting impedance signal.

13. A non-transitory computer-readable medium encoded with programming instructions for measuring an electrical bio-impedance of a patient with an implantable medical device comprising a voltage source that provides available voltage headroom, a current pulse generator that operates at an operating voltage, a control unit that operates said current pulse generator, a determination unit, and at least one electrode configuration, said programming instructions causing:
said control unit, in an electrical bio-impedance measurement to operate said current pulse generator, to generate at least one impedance measurement signal having at least one asymmetric multiphasic waveform comprised of a plurality of pulse phases each having a pulse phase amplitude, with respect to said operating voltage, and a pulse phase width, said waveform a waveform amplitude that is asymmetric with respect to said operating voltage, and said waveform having an overall DC component that is substantially equal to 0, the asymmetry of said waveform amplitude allowing substantially all of said available voltage headroom to be used by said impedance measurement signal, and to apply said at least one impedance measurement signal with said waveform to said patient using said at least one electrode configuration and to detect at least one resulting impedance signal produced by the application of said at least one impedance measurement signal with said waveform as a measured impedance signal; and
said determination unit to determine at least one impedance value from the measured impedance signal.

* * * * *